US005245988A

United States Patent [19]

[11] Patent Number: 5,245,988

[45] Date of Patent: Sep. 21, 1993

Einars et al.

[54] PREPARING A CIRCUIT FOR THE PRODUCTION OF SHOCKWAVES

[75] Inventors: Wolfram Einars, Neukeferloh; Harald Eizenhoefer, Munich; Reiner Schultheiss, Echling, all of Fed. Rep. of Germany

[73] Assignee: Dormer GmbH, Fed. Rep. of Germany

[21] Appl. No.: 614,386

[22] Filed: Nov. 14, 1990

[30] Foreign Application Priority Data

Nov. 15, 1989 [DE] Fed. Rep. of Germany ....... 3937904

[51] Int. Cl.[5] ............................................ A61B 17/22

[52] U.S. Cl. .............................. 128/24 EL; 181/120; 367/147

[58] Field of Search ....................... 181/118, 120, 142; 315/175, 176, 171; 372/86; 367/141, 147; 128/24 EL

[56] References Cited

U.S. PATENT DOCUMENTS 4,834,074 5/1989 Reichenberger .............. 128/24 EL
4,928,671 5/1990 Reichenberger et al. ..... 128/24 EL
4,962,753 10/1990 Cathignol et al. ................ 367/147
5,095,891 3/1992 Reitter ........................... 606/128 X
5,105,801 4/1992 Cathigrol et al. .................. 181/118

FOREIGN PATENT DOCUMENTS 0400294 12/1990 European Pat. Off. ....... 128/24 EL
3150430 7/1983 Fed. Rep. of Germany ... 128/24 EL
3627168 2/1988 Fed. Rep. of Germany ... 128/24 EL
3737859 4/1989 Fed. Rep. of Germany ... 128/24 EL
3804993 8/1989 Fed. Rep. of Germany ... 128/24 EL

*Primary Examiner*—Lee S. Cohen
*Assistant Examiner*—Krista M. Pfaffle
*Attorney, Agent, or Firm*—Ralf H. Siegemund

[57] ABSTRACT

The ignition of spark gaps for the production of shockwaves in the contactless comminution of concrements, using a capacitor discharge is improved by providing at least for some time prior to the ignition proper a voltage much smaller than the breakthrough voltage for producing a small current between the electrodes that prepares a channel in the discharge gap.

2 Claims, 1 Drawing Sheet

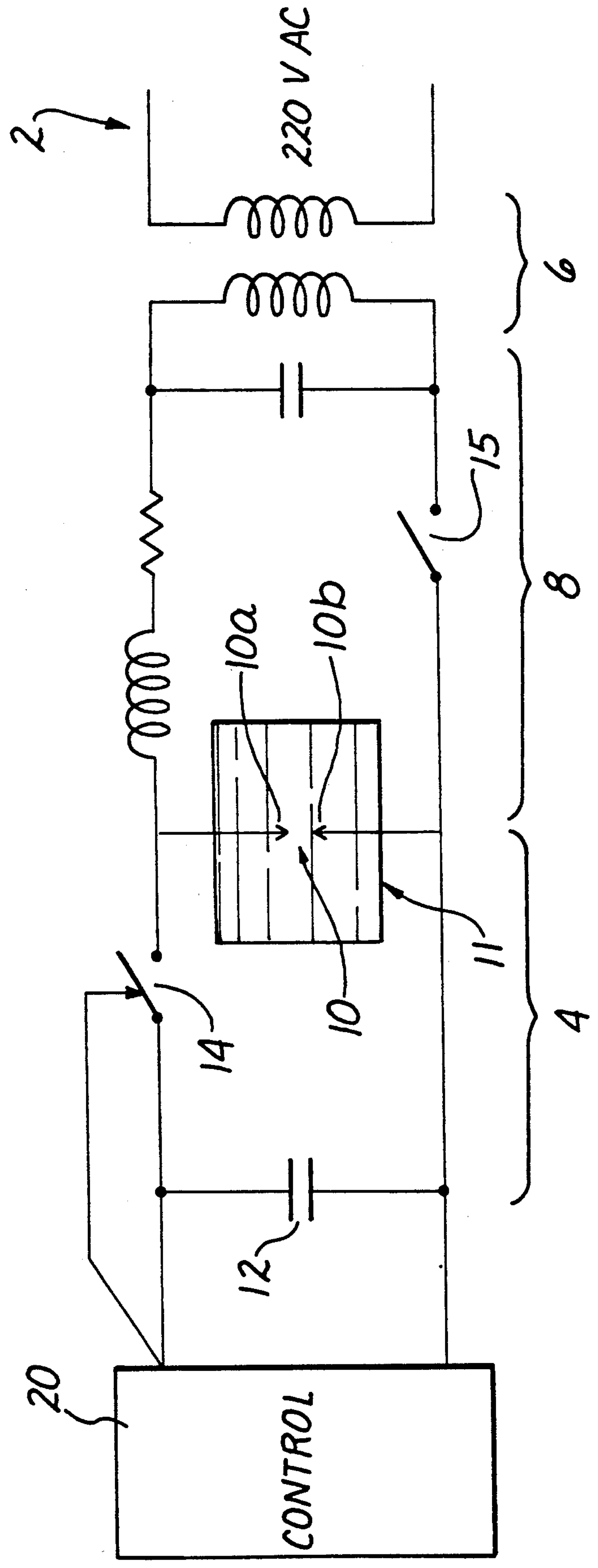
2
220 V AC
6
15
8
10a
10b
10
11
4
14
12
20
CONTROL

PREPARING A CIRCUIT FOR THE PRODUCTION OF SHOCKWAVES

BACKGROUND OF THE INVENTION

The present invention relates to improvements in the ignition of sparks between electrodes defining a gap and more particularly the invention relates to the improvement in the operation of underwater spark gaps used for the production of shockwaves serving for the contact-free comminution of concrements in the body of living beings.

Shockwave sources are used in a variety of medical and technical equipment. Here particularly shockwaves have been found highly suitable in shockwave lithotripsy for the noninvasive destruction of concrements in the body of living beings. Basically electrical energy stored in a capacitor is discharged in an underwater spark gap and on the production of the discharge spark or arc the local sudden heating produces shockwaves. The shockwaves are then focused towards a concrement, pass through the skin of the patient and combine in the focal point of the equipment that has been oriented to coincide with a concrement. The concrements are reduced in this fashion to small gravel and fractions and can then be discharged through normal physiological process.

The shockwave focusing is usually carried out under utilization of a reflecting rotational ellipsoid having two focal points; one of them contains (or straddles) the spark gap and the other one is positioned to coincide with the concrement in the person. U.S. Pat. No. 3,942,531 as well as the German patent 26 35 635 shows various forms of the spark gap. For further reference see also U.S. Pat. Nos. 4,809,682, 4,940,050, 4,905,673, 4,938,781.

Considering some details of a discharge into a gap, the path of the arc in the gap is determined through a near currentless path of a so called leader. This leader is particularly a channel between the two electrodes and is produced in the instant of applying a high voltage between the electrodes but prior to the actual current flow and that leader then determines the current flow that forms the spark and is the actual arc. The leader is primarily determined by the field gradients and field lines between the positive and negative electrodes. But local variations on account of the presence for example of water or the like determines considerably the local detailed path configuration of that leader. In other words, a straight line between say the electrode tips is more or less an average path approximation. The electrical field needed between the electrodes for producing an adequate shockwave that is sufficient for the destruction of concrements could lead to thermal breakthrough characterized by certain delays in the ignition lasting from 1 microsecond up to a millisecond as between the ignition triggering and the actual spark depending on the voltage, the effective conductivity in the distance and other geometric factors. The relatively large temporal spread is attributed to the fact that the growth and propagation of the leader is a stochastic process, but that spread in the delay results in significant variations in the level of shock wave production.

DESCRIPTION OF THE INVENTION

It is an object of the present invention to provide a new and improved method by means of which the formation of the leader channel in an arc gap can be reduced in terms of time and energy to thereby reduce the spread which in turn will be effective as a longer use life of the electrode.

It is therefore a particular object of the present invention to provide a new and improved method for ignition of spark gaps having two facing electrodes and used for the production of shockwaves to serve the contactfree comminution of concrements in the body of living beings.

It is a further object of the invention to improve lithotripters having an underwater spark gap whose electrodes are connectible at times to a store of electrical energy, such as a capacitor, which discharges through the gap.

In accordance with the preferred embodiment of the present invention the object and the particular and further objects are attained by using a supplemental circuit providing at least prior to the capacitor discharge and main spark production, a voltage between the electrodes which is considerably smaller than the breakthrough voltage and causes a very small electric current to flow between the electrodes. That voltage is permanently effective on the arc gaps or is applied just prior to the application of the main breakthrough voltage. The voltage is either AC or DC. The ignition of course obtains by applying a high voltage to the electrodes which then directly affects formation of arc across the then prepared channel.

Turning now to some details an underwater arc discharge results in the production of shockwaves which in turn provides for some erosion of the electrode tips. This is in addition to possible burn off of these tips. Together these deteriorating effects establish that the effective distance between the electrodes increases which means that the local field strength between the electrodes for the same high voltage drops. The ignition delay that occurs between the application of a high voltage to the electrodes and the collapse thereof as the electrical energy stored in the capacitor flows into the electrodes can be a certain charge to flow off the capacitor prior to ignition proper and that this in fact reduces the available energy for the spark producing breakthrough. The shorter the ignition delay the larger the energy in the capacitor which remains for the discharge proper.

During the normal ignition delay a certain current density has to be maintained between the electrodes for purposes of producing an arc discharge channel to which the high voltage will then cause current to flow until thermal breakthrough occurs. The current density distribution is directly proportional to the field strength distribution assuming homogeneous and location independent conductivity. The field strength distribution on the other hand is determined through the geometry involved so that the particular properties of all the participating materials, electrically conductive ones as well as insulating ones, are determining factors and finally the discharge is of course determined by the voltage that is applied. The voltage however is a variable one on account of the variable delay on one hand and the fixed initial charge on the capacitor on the other hand.

It can be seen further that the current density distribution should be limited to a narrow channel which will then contain the leader producing the breakthrough. The current density distribution can be kept confined to a narrow channel if the field strength or the conductivity or both is limited and restricted to a very narrow region around an axis that extends between the electrodes. This is what the invention accomplishes.

In accordance with the invention the current distribution is determined in that the conductivity is increased locally in the region between the electrode tips through the resulting temperature distribution. It is produced by providing for local heating through a permanent or pulsed electric current. That current produces locally hydrolysis so that near the electrode surface small gas bubbles obtain which one very beneficial to the production of the leader. As stated dc or ac voltage is applied permanently to the electrodes leading to currents in the range between 10 and 100 microamps. Hence a permanent current distribution and density is produced across the gap between the electrodes. This electrolytic current produces effects so that the water dipoles are oriented in that region while a certain electrolysis obtains on the electrode surfaces. The energy and time expenditure for the production of a conductive plasma channel is in effect reduced by this approach.

At the time of actual discharge of the capacitor a higher amount of charge is actually available because that charge is not drawn on for the generation of the initial channel. This in turn makes sure that the resulting shockwave has a higher intensity. Primarily the temporal spread in the ignition as far as the delay is concerned is reduced. That in turn results in a spark and a shockwave production of a more uniform intensity, quite uniform in amplitude i.e. the spread in the variation is reduced. Since the channel is narrowed to an axial region between the electrodes around the focal point of the rotational ellipsoids that reflects the shockwave, the so called imaging errors will be reduced. In other words the shockwaves as produced will in fact be focused right at the second therapeutic focal point. That in turn reduces the statistical scatter and spread in shockwave intensity in the therapeutic focal point.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 illustrates a circuit diagram for practicing the preferred embodiment of the present invention in a best mode environment.

Proceeding now to the detailed description of the drawings, the figure includes a spark gap 10 provided by two electrodes 10*a* and 10*b* of the kind and configuration as shown for example in the various references alluded to above. The spark gap 10 is submerged in a water filled chamber 11 so that upon an arc discharge between the electrodes 10*a, b* a shockwave is produced. For normal operation this electrode pair belongs to a shockwave circuit 4 and through a switch 14 these electrodes can be connected to a discharge capacitor 12 so that the capacitor will discharge through these electrodes. The reference numeral 20 refers generally to the control of the charging of the capacitor 12 and may include control devices for closing the switch 14 whenever the production of the shockwave is desired. Thus far this is conventional technology which is adapted herein.

For practicing the invention in a particular way the shockwave circuit 4 supplemented as follows. Reference numeral 2 refers generally to a voltage supply which may be 220 or 110 V AC and may be part of the power supply that powers the equipment. Transformer 6 reduces the voltage to a more suitable level and can be regarded as being included in a current limiting circuit 8 for purposes of protecting that particular circuit from transient high voltage pulses that may obtain when the switch 14 closes. This current limiting circuit 8 provides a current into the electrode gap 10 on a permanent basis to produce the channel between the two electrodes 10*a* and 10*b* to reduce the ignition delay and to reduce the delay to break through following closing of switch 14. In lieu of the ac circuit one can use a battery or another suitable low voltage power supply.

By way of example the electrode 10*a* and 10*b* may be spaced by 2.4 mm from each other and the voltage from the capacitor 12 to be applied to the electrodes is about 14 kvolts. The capacitor 12 is assumed to have 80 nanofarads. The circuits 6 and 8 together produce a perpetuating current in the gap 10 of 30 milliamps which reduces the ignition delay from roughly 130 microseconds down to 30 microseconds. The voltage available on capacitor 12 at the instant of ignition is still about 90% of the original voltage as compared with the voltage drop to about 30% in the known devices. Aside from the gain in energy it is important that the ignition is more reliable and even if for other reasons the voltage is dropped the electrodes last much longer.

The invention as shown provides for a permanent connection of the circuit 6,8 to the electrodes 10*a* and 10*b* but conceivably there may be an additional switch 15 interposed e.g. The input circuit 2 may be correlated to an additional switch 14, in that the switch 15 closes the circuit for this auxiliary and preparatory process just a little ahead of the closing of the switch 14. The formation of the channel is of course a matter of very short periods of time.

The invention is not limited to the embodiments described above but all changes and modifications thereof, not constituting departures from the spirit and scope of the invention, are intended to be included.

We claim:

1. In a method of improving shockwave lithotripsy using a liquid-submerged ignition of an arc discharge gap in a lithotripter which includes electrodes submerged in such a liquid for the production of shockwaves to be used in the contactless comminution of concrements, wherein the lithotripter further includes a capacitor, and the method includes a step of selectably connecting the capacitor to the electrodes, thereby causing the capacitor to be discharged across the electrodes for the production of the shockwaves, the improvement comprising;

providing to the electrodes at least for some time prior to the step of connecting the capacitor to the electrodes for the application of a capacitor voltage to the electrodes, a considerably smaller voltage than a breakthrough voltage for the electrodes; and producing by the said providing step a small, preparatory electric current between the electrodes, the current as so provided being smaller than a current that flows between the electrodes after a full capacitor voltage has been applied to the electrodes, for preparing a channel in the liquid of the arc discharge gap to be effective immediately upon discharge of said capacitor.

2. In a lithotripter, a circuit having a pair of electrodes in a water bath for the production of shockwaves, the circuit further including a capacitor discharge circuit, and a switch means for connecting said capacitor discharge circuit to said electrodes, the improvement comprising, a low voltage circuit; and means for connecting the low voltage circuit to the electrodes prior to closing said switch means and providing a voltage to the electrodes that is significantly smaller than a breakthrough voltage between the electrodes in the water bath, so that a low level, channel-forming electric current flows through the water both between the electrodes.

* * * * *